United States Patent
Chang et al.

(10) Patent No.: US 9,555,398 B2
(45) Date of Patent: Jan. 31, 2017

(54) METHANE SYNTHESIS CATALYST PREPARATION METHOD AND CATALYST PRECURSOR

(75) Inventors: Junshi Chang, Beijing (CN); Jianming Jiang, Beijing (CN); Yingqiu Guo, Beijing (CN); Donghui Ci, Beijing (CN); Jianxiang Zhang, Beijing (CN); Zhixiang Lei, Beijing (CN); Pengxiang Liu, Beijing (CN); Shuying Sun, Beijing (CN); Jianping Song, Beijing (CN); Junjun Du, Beijing (CN)

(73) Assignee: XINDI ENERGY ENGINEERING TECHNOLOGY CO., LTD., Langfang, Hebei (CN)

( * ) Notice: Subject to any disclaimer, the term of this patent is extended or adjusted under 35 U.S.C. 154(b) by 769 days.

(21) Appl. No.: 13/994,243

(22) PCT Filed: Dec. 14, 2011

(86) PCT No.: PCT/CN2011/083949
§ 371 (c)(1),
(2), (4) Date: Sep. 19, 2013

(87) PCT Pub. No.: WO2012/079505
PCT Pub. Date: Jun. 21, 2012

(65) Prior Publication Data
US 2014/0031199 A1    Jan. 30, 2014

(30) Foreign Application Priority Data

Dec. 15, 2010    (CN) .......................... 2010 1 0605823

(51) Int. Cl.
*B01J 23/58* (2006.01)
*B01J 23/78* (2006.01)
(Continued)

(52) U.S. Cl.
CPC ............... *B01J 23/78* (2013.01); *B01J 23/005* (2013.01); *B01J 23/755* (2013.01); *B01J 37/08* (2013.01);
(Continued)

(58) Field of Classification Search
CPC .......... B01J 23/78; B01J 37/08; B01J 23/005; B01J 37/16; B01J 23/755; C07C 1/12; C07C 1/10
(Continued)

(56) References Cited

U.S. PATENT DOCUMENTS 4,713,300 A * 12/1987 Sowman ................ B01D 39/20
427/102

FOREIGN PATENT DOCUMENTS

CN    101391218 A        3/2009
CN    101433863 A *      5/2009
(Continued)

OTHER PUBLICATIONS

Garcia et al. "Hydrogen Production by Steam Gasification of Biomass Using Ni—Al Coprecipitated Catalysts Promoted with Magnesium" Energy Fuels, 2002, 16 (5), pp. 1222-1230, Jul. 25, 2002.*

(Continued)

*Primary Examiner* — Colleen Dunn
*Assistant Examiner* — Haytham Soliman
(74) *Attorney, Agent, or Firm* — Steven B. Phillips; Moore & Van Allen PLLC

(57) ABSTRACT

The present invention relate to a methane synthesis catalyst preparation method, comprising a preparation step for a catalytic body and a prereduction step. The prereduction step comprises: calcining the catalytic body to form a nickel aluminate spinel-containing catalyst precursor; and prereducing the catalyst precursor to acquire the methane syn-
(Continued)

thesis catalyst. The catalyst prepared in the preparation method can be used in high-temperature and high liquid-to-gas ratio conditions, shows performance stability, and obviates the need for a further step of high-temperature reduction during vehicle operation. Also provided is the methane synthesis catalyst precursor. The catalyst precursor contains nickel aluminate spinel.

9 Claims, 2 Drawing Sheets

(51) Int. Cl.
*B01J 23/00* (2006.01)
*B01J 23/755* (2006.01)
*B01J 37/16* (2006.01)
*C07C 1/10* (2006.01)
*C07C 1/12* (2006.01)
*B01J 37/08* (2006.01)

(52) U.S. Cl.
CPC ............... *B01J 37/16* (2013.01); *C07C 1/10* (2013.01); *C07C 1/12* (2013.01)

(58) Field of Classification Search
USPC .......................................................... 502/238
See application file for complete search history.

(56) References Cited

FOREIGN PATENT DOCUMENTS

| CN | 102125849 A | 7/2011 |
|---|---|---|
| GB | 2188251 A | 9/1987 |

OTHER PUBLICATIONS

Machine Translation of Cho et al., CN 101433863 A May 20, 2009.*
Enn Xinneng (Beijing) Technology Co., Ltd., International Application No. PCT/CN2011/083949, International Search Report, Feb. 13, 2012.
Murthy, I.A.P.S., Catalytic behaviour of NiAl2O4 spinel upon hydrogen treatment, Journal of Materials Science, 1993, vol. 28, pp. 1194-1198.

* cited by examiner

METHANE SYNTHESIS CATALYST PREPARATION METHOD AND CATALYST PRECURSOR

TECHNICAL FIELD

The present invention relates to the field of methanation of oxycarbides, in particular to a methane synthesis catalyst preparation method and catalyst precursor.

BACKGROUND ART

In the methane synthesis catalyst system, a nickel-based catalyst is essential since it has a better catalytic activity and has an activity being next only to ruthenium catalyst. In the methane synthesis catalyst commonly used at domestic and abroad, the active component nickel is present mostly in the form of nickel oxide. Nickel present in the form of nickel oxide can be readily reduced, and most of nickel in an oxidation state will be reduced at 450° C. However, the action between nickel and the support is too weak to be sintered and inactivated at high temperatures and high liquid to steam ratio.

The reduction equation is stated as follows:

$$NiO+H_2 \leftrightarrow Ni+H_2O+3.52 \text{ KJ/mol}$$

Thus a novel method for preparing a catalyst needs to be provided.

CONTENTS OF THE INVENTION

In order to make improvement regarding sintering and inactivation, the applicant developed a high temperature resistant and hydration resistant catalyst containing a nickel aluminate spinel prior to the prereduction. Before prereduction, nickel is primarily present in the form of a spinel structure. The so-called spinel is a solid having a homogeneous composition formed by nickel and alumina via the solid phase reaction and diffusion during the calcining process. The chemical formula thereof is $NiAl_2O_4$ and belongs to the cubic system. The unit cell thereof is comprised of 32 cubic close packing oxygen anions $O^{2-}$, 16 aluminum ions $Al^{3+}$ in the octahedral interstice and 8 nickel ions $Ni^{2+}$ in the tetrahedral interstice. Oxygen has 4 metal coordinations, wherein three of them are inside the octahedron, and the remaining one is inside the tetrahedron. The saturated structure of the nickel aluminate spinel enables nickel to be in much contact with the body and to have a strong acting force. After the metallic nickel is reduced from the spinel, it generally has a homogeneous diffusion, a high dispersion degree, a small grain size, a high activity and is not easy to be sintered and inactivate at high temperatures and high liquid to steam ratio. However, a higher temperature, generally higher than 700° C. is required to reduce nickel in the spinel state.

Reduction at such high reduction temperature will cause the following several problems.
1. High reduction temperature, long period of heating time, causing a long period of operation cycle, a low production efficiency and increasing the operation risk;
2. the reduction temperature being higher than the reaction temperature, so as to have more strict requirements on the selection of the devices, which will necessarily increase the investment cost;
3. the electric heater prior to the reactor needs to have a very high power so as to heat to the required reduction temperature; during the subsequent reaction phase, the heat released from the methane synthesis reaction is sufficient to maintain the temperature required by the reaction, so that the electric heater is almost in an idle state to cause severe resource wasting.

In order to solve the problems above, the inventor of the present invention surprisingly found that the following method for preparing the catalyst not only can ensure the performance of the catalyst, but also can solve the problem of reduction at high temperature. For example, a catalytic body was prepared by the mixing-precipitation method or co-precipitation method, calcined at high temperature during the prereduction to form a nickel aluminate spinel-containing catalyst precursor, then prereduced, so as to save much energy sources and increase the production efficiency. Meanwhile, the catalyst is desulfurized during the prereduction to remove the elemental sulfur brought from the raw material during the preparation of the catalyst, and to eliminate a hidden danger of sulfur poisoning of the catalyst.

Thus one aspect of the present invention is to provide a method for preparing a methane synthesis catalyst, comprising a preparation step for a catalytic body and a prereduction step, wherein the prereduction step comprises calcining the catalytic body to form a nickel aluminate spinel-containing catalyst precursor; and prereducing the catalyst precursor to acquire the methane synthesis catalyst.

According to a certain preferred embodiment, the preparation step for a catalytic body comprises spray drying a slurry containing nickel nitrate, aluminium hydroxide and light magnesium oxide.

According to a certain preferred embodiment, the preparation step for a catalytic body comprises neutralizing with an aluminium-containing precipitator a suspension or solution containing nickel nitrate and a magnesium compound selected from the group consisting of magnesium nitrate and light magnesium oxide. According to a certain preferred embodiment, the aluminium-containing precipitator is sodium metaaluminate. According to a certain preferred embodiment, the calcining step is carried out at 700-1000° C.

According to a certain preferred embodiment, the calcining step comprises using a $N_2$ replacement system to ensure that $O_2$ in the system is in an amount of equal to or less than 0.5 vol. %, maintaining the system pressure to be 0.01-0.05 MPa according to the pressure gauge, the space velocity being 50-100 $h^{-1}$, heating to 120-130° C. at a rate of 50-70° C./h, maintaining the temperature for 2-5 h to clean out the physically absorbed water, continuing to heat to 250° C. at a rate of 30-70° C./h, maintaining the temperature for 2-5 h to clean out the crystalline water, continuing to heat to 700-1000° C. at a rate of 10-70° C./h, maintaining the temperature for 3-6 h to form a nickel aluminate spinel-containing catalyst precursor.

According to a certain preferred embodiment, the preparation step for a catalytic body comprises formulating an aqueous solution of nickel nitrate; adding light magnesium oxide or magnesium nitrate hexahydrate into said aqueous solution of nickel nitrate, heating to 40-80° C. at a stirring rate of 80-250 r/min to acquire a suspension or solution; neutralizing with sodium metaaluminate as a precipitator a suspension or solution to obtain a precipitate; and drying the precipitate at 110-140° C. for 12-24 hours to obtain a catalytic body. According to a certain preferred embodiment, the prereduction step further comprises the step of desulfurizing the catalyst. According to a certain preferred embodiment, the desulfurizing step comprising detecting the sulfur content in the reduction gas of the system while the reaction temperature in the prereduction reactor reaches 650-750° C., the gas being switched to a thionizer if the volume content of sulfur in the reduction gas of the reduction system is equal to or less than 0.1 ppm, desulfurizing at a temperature less than 800° C. for 10-12 h so as to desulfurize the catalyst.

According to a certain preferred embodiment, the methane synthesis catalyst, comprises, in mass percent, 40-80% of $Al_2O_3$, 10-30% of Ni, and 10-30% of MgO.

According to a certain preferred embodiment, the prereduction step is conducted in a prereduction reactor at 700-1100° C., a system pressure of 0.05-0.1 MPa and a space velocity of 100-800 $h^{-1}$. Preferably, the prereduction reactor is a cylindrical reactor having an aspect ratio of 1.5/1 to 5/1.

According to a certain preferred embodiment, the method of the present invention further comprises the following terminate steps of reducing the internal temperature inside the prereduction reactor, replacing with $N_2$ the reduction gas in the reactor while the internal temperature in the prereduction reactor is lowered to less than 50° C., to make the volume content of $H_2$ in the reactor equal to or less than 0.5%; feeding $O_2$ till $O_2$ is in a volume amount of 0.1-0.2% of the total gas in the reactor, while maintaining the temperature inside the prereduction reactor not more than 50° C.; feeding air and maintaining the temperature inside the reactor not more than 50° C. till the oxygen content at the inlet of the reactor is consistent with the oxygen content at the outlet of the reactor.

According to the method for preparing a methane synthesis catalyst in a certain embodiment, $H_2/N_2=1/10-10/1$ by volume during the prereduction in the system.

The second aspect of the present invention is to provide a methane synthesis catalyst precursor, wherein the catalyst precursor comprises a nickel aluminate spinel.

According to the catalyst precursor in a certain embodiment, the nickel aluminate spinel is in a mass content of 5-75% in the precursor.

Figure 1:
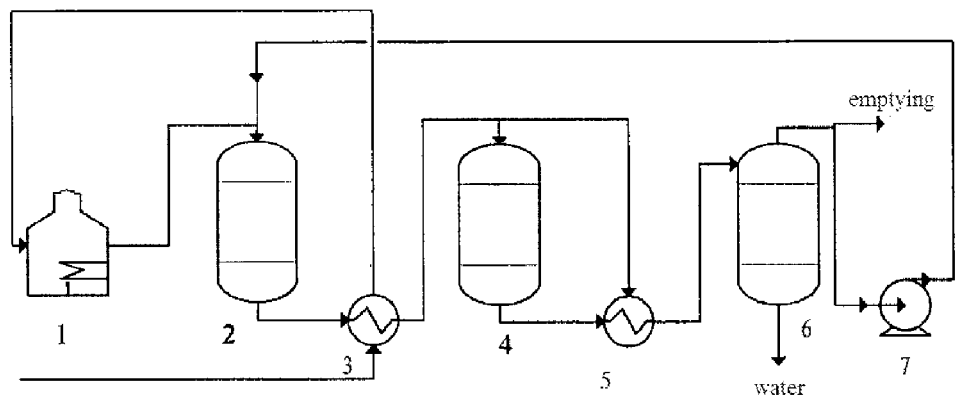
FIG. 1 shows the flow diagram of the prereduction of a nickel aluminate spinel-containing catalyst.

1—heating furnace; 2—prereduction reactor; 3—heat exchanger; 4—thionizer; 5—water condenser; 6—water separator; 7—circulation compressor

EMBODIMENTS

Unless otherwise specified, in this invention, the term "catalytic body" represents a catalyst composition not calcined at high temperatures, i.e. the state of the target catalyst product prior to calcination at high temperatures. To be more specific, it represents an existing form of the target catalyst product before the formation of a nickel aluminate spinel-containing catalyst precursor by calcination at high temperatures in the present invention.

The term "catalyst precursor" represents a catalyst composition which is not reduced, i.e. the state of the target catalyst product prior to reduction. To be more specific, it represents a nickel aluminate spinel-containing composition obtained by calcining the catalytic body at high temperatures during the prereduction.

The term "prereduction" represents the process of reducing with hydrogen or other reductive gases fresh catalyst at a certain temperature to active metal or suboxides. The generally called reduction represents the activation process, is mostly conducted in a reactor of the application factory, and in a catalyst production factory sometimes, which may be called prereduction. In the catalyst production process of the present invention, the catalytic body is calcined at high temperatures under the nitrogen atmosphere to form a nickel aluminate spinel-containing catalyst precursor. At a suitable temperature, nickel in the nickel aluminate spinel-containing catalyst precursor is reduced with a mixed gas of hydrogen and nitrogen to a low valent nickel or metallic nickel.

The term "coke oven gas" represents an inflammable gas produced together with coke and tar product after several bituminous coals are formulated into oven coal and dry distilled at high temperatures in a coke oven, and is a by-product of coking industry. After purification, the main ingredients thereof are stated as follows.

| Name | CH4 | $C_2H_6$ | $N_2$ | $CO_2$ | CO | $O_2$ | $H_2$ |
|---|---|---|---|---|---|---|---|
| Composition (Mol. %) | 23-27 | 2-4 | 3-7 | 1.5-3 | 5-8 | 0.3-0.8 | 55-60 |

The process of the preparation method for the catalytic body is illustrated as follows.

I. Mixing-Precipitation Method

Firstly, the amount of each substance is calculated according to the mass percent of each component in the catalyst. A certain amount of nickel nitrate hexahydrate is weighed; a certain amount of distilled water is added to dissolve into a nickel nitrate solution. A certain amount of aluminium hydroxide and light magnesium oxide are then weighed and added into said nickel nitrate solution, to homogeneously stir to form a slurry, to spray dry at an outlet temperature of 120-140° C. of the spray drier and mold (e.g. sheet beating) to obtain a catalytic body. Before use, such body is prereduced (the specific operations of the prereduction are as follows).

In the catalyst prepared after prereduction, the mass percent of each component is as follows: 40-80% of $Al_2O_3$, 10-30% of Ni, and 10-30% of MgO.

II. Co-Precipitation Method

A certain amount of nickel nitrate hexahydrate is weighted; a certain amount of distilled water is added to dissolve into a nickel nitrate solution. A certain amount of light magnesium oxide and magnesium nitrate hexahydrate are then weighed and added into said nickel nitrate solution, heated to 40-80° C. at a stirring rate of 80-250 r/min. Sodium metalluminate in a certain concentration is used as the precipitator to neutralize said suspension or solution. The sodium metalluminate solution shows a strong basicity, and does not need the addition of aluminium-containing raw materials as compared with the common precipitator, so as to increase the production efficiency. Moreover, the less the categories of the raw material are, the more homogeneous the mixing of nickel and aluminium is. After filtering, rinsing, drying, pulverizing, molding by the common methods, e.g. sheet-beating or extrusion molding, a catalytic body is obtained. Before use, such body is prereduced (the specific operations of the prereduction are as follows).

In the catalyst prepared after prereduction, the mass percent of each component is as follows: 40-80% of $Al_2O_3$, 10-30% of Ni, and 10-30% of MgO.

The specific operations of the prereduction are illustrated as follows.

A catalytic body was fed into a cylindrical prereduction reactor 2 having an aspect ratio of 1.5/1 to 5/1, which was used to shorten the residence time of the vapor concentration in the catalyst bed layer as much as possible. A $N_2$ replacement system was used to ensure that $O_2$ in the system is in an amount of equal to or less than 0.5 vol. %, and to maintain the system pressure to be 0.01-0.05 MPa according to the pressure gauge. A compressor 7 was initiated to enable the space velocity to be 50-100 $h^{-1}$. The temperature was heated at a rate of 50-70° C./h. The temperature in the prereduction reactor was heated to 120-130° C. and maintained for 2-5 h to clean out the physically absorbed water, then heated to 250° C. at a rate of 30-70° C./h and maintained for 2-5 h to clean out the crystalline water, heated to 700-1000° C. at a rate of 10-70° C./h and maintained for 3-6 h to enable the solid phase reaction between nickel oxide and alumina to occur and to form a nickel aluminate spinel-containing catalyst precursor.

The temperature was then decreased at a rate of 5-8° C./h. When the temperature inside the prereduction reactor 2 ranged from 600-650° C., hydrogen was used to replace nitrogen in the system to enable the pressure (gauge pressure) in the system to be 0.05-0.1 MPa. The circulation was increased to achieve a space velocity of 100-800 $h^{-1}$. After $H_2/N_2$=1/10 to 10/1 (volume ratio), the temperature continued to be increased at a rate of 10-70° C./h. When the reaction temperature reached 650-750° C., the sulfur content in the system was detected; when the sulfur content was equal to or greater than 0.1 ppm (by volume), the gas was switched into a thionizer 4 fed with a fine desulfurizer, e.g. ZnO, and desulfurized at a temperature of less than 800° C. for 10-12 h and fed into a water condenser 5. If the sulfur content was equal to or less than 0.1 ppm (by volume), the gas was directed switched into the water condenser 5.

Finally, the temperature in the prereduction reactor 2 was maintained at 700-1100° C. for 2-24 h, wherein most of nickel was reduced. Then the temperature was decreased at a rate of 5-20° C./h. When the temperature inside the prereduction reactor is less than 50° C., $N_2$ was used to replace $H_2$ in the system to enable the volume percent of $H_2$ in the system to be equal to or less than 0.5%. Then $O_2$ was fed in an amount of 0.1-0.2 vol. % of the total gas amount in the system. The temperature increase was observed to ensure the temperature in the prereduction reactor to be not more than 50° C. The $O_2$ concentration was gradually increased till the temperature in the prereduction reactor was not more than 50° C. even if $O_2$ was fed. Meanwhile, after the oxygen content at the inlet of the reactor is consistent with that at the outlet, the passivation operation ends, and the prereduction also ends.

In the aforesaid technological operation, the technological process is described as follows.

The supplemental reduction gas was fed into a heat exchanger 3, and heat exchanged with the residual gas after reduction, and then fed into a heating furnace 1 for further heating, and then fed into the reactor for reduction. The residual gas was discharged from the bottom of the reactor, fed into the heat exchanger 3 and heat exchanged with cold supplemental reduction gas for temperature decrease. An analysis point was set up herein for detecting the sulfur content in the system after the temperature in the prereduction reactor reached 650-750° C. Since sulfate radical may be introduced during the preparation of the catalyst, sulfur in the sulfate radical will be reduced when the reaction temperature reached 650-750° C. under the hydrogen circumstance. When the sulfur content was equal to or greater than 0.1 ppm (by volume), the gas was switched into a thionizer 4 fed with a fine desulfurizer, e.g. ZnO, and desulfurized at a temperature of less than 800° C. for 10-12 h and fed into a water condenser 5. If the sulfur content was equal to or less than 0.1 ppm (by volume), the gas was directed switched into the water condenser 5, decreased to 50° C. and fed into the water separator 6. After water was separated therefrom, a part of water was emptied, and a part of water was recycled via a circulation compressor 7 to the prereduction rector for further reduction, which saves a large amount of the reduction gas. 4 temperature points were homogeneously and radially set up in the prereduction reactor, and a temperature point was set up axially each half a meter so as to ensure homogeneous temperature in the reactor. Upon analysis by X-ray diffractometer, the reduced homojunction nickel had a grain size of (111) face 5.0 to 15.0 nm, nickel (200) face 5.0-15.0 nm and nickel (200) face 5.0-15.0 nm.

The analysis and detection methods used in the present invention are as follows:
1. Crystalline phase and grain size of nickel in the catalyst and the catalyst precursor was analyzed with D/max-2200PC X-ray diffractometer (XRD) made by Rigaku, Japan.
2. The catalyst components were analyzed with Optima2100DV inductive coupling plasma emission spectrograph, PE, U.S.A.
3. A thermogravimetric analysis (DTG) of the catalyst phase transition and carbon accumulationn was conducted with Netzsch STA449F3 thermoanalyzer.
4. The product composition was analyzed according to the GB/T 13610-2003 with 6890N gas chromatography, Agilent, U.S.A.

The present invention is further described by combining with the drawings of the description. The following examples are merely the preferred examples, and cannot be used to define the scope of the invention. That is to say, any change and modification made according to the patent scope of the present application for invention will fall within the scope of the present invention patent. Unless otherwise specified, any percent content, ratio or part involving the gas in this invention is in volume, and any percent content, ratio or part involving the solid and liquid is in weight.

Example 1

The Catalyst Having a Composition of, in Mass Percent, 60% of $Al_2O_3$, 20% of Ni, and 20% of MgO 40 kg of nickel nitrate hexahydrate was weighted, and 40 L of distilled water was added to stir constantly until nickel nitrate hexahydrate was completely dissolved. 32 kg of aluminium hydroxide and 8 kg of light magnesium oxide were weighed and added to said nickel nitrate solution, homogeneously stirred to form a slurry and dried with a spray drier, wherein the temperature at the outlet was 130° C. The dried nickel nitrate and aluminium hydroxide were decomposed to oxides, and sheet beaten to a catalytic body. Then the catalytic body was fed into a cylindrical reactor having an aspect ratio of 2/1. A $N_2$ replacement system was used to ensure that $O_2$ in the system is in an amount of equal to or less than 0.5 vol. %, and to maintain the system pressure to be 0.01-0.05 MPa according to the pressure gauge. A compressor 7 was initiated to enable the space velocity to be 50 $h^{-1}$. The temperature was heated at a rate of 50° C./h. The temperature in the prereduction reactor was heated to 120-130° C. and maintained for 3 h to clean out the physically absorbed water, then heated to 250° C. and maintained for 3 h to clean out the crystalline water, heated to 700° C. at a rate of 30° C./h and maintained for 3-6 h to enable the solid phase reaction between nickel oxide and alumina to occur and to form a nickel aluminate spinel-containing catalyst precursor.

Figure 2:
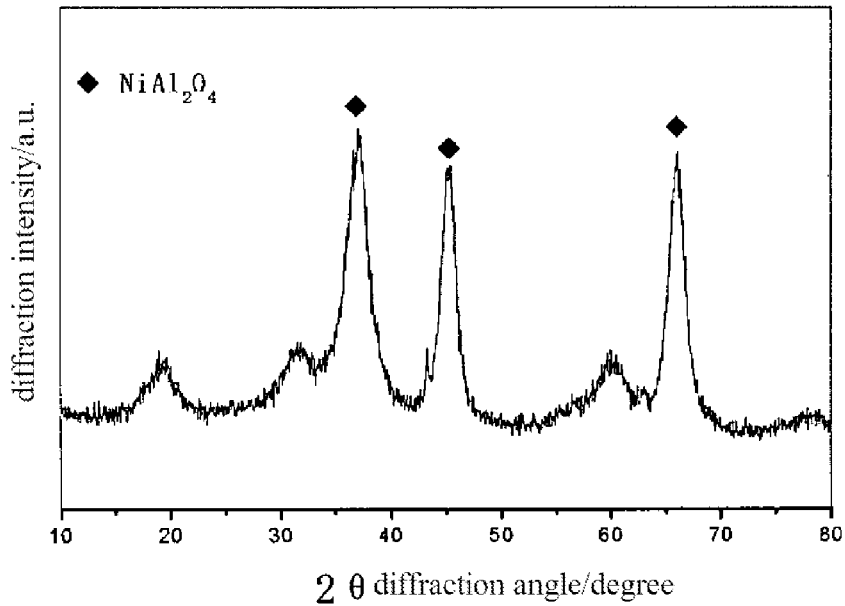
FIG. 2 shows the XRD pattern of the catalyst precursor calcined at high temperature in Example 1.

FIG. 2 shows the XRG pattern of the catalyst precursor calcined at high temperature. Thus the characteristic peaks of the nickel aluminate spinel occur, and the nickel aluminate spinel is in a mass percent of 5% in the precursor. The diffraction angles of the nickel aluminate spinel are respectively 37°, 45.1° and 65.7°.

The temperature was then decreased at a rate of 6° C./h. When the temperature inside the prereduction reactor 2 was 600° C., hydrogen was used to replace nitrogen in the system so that the pressure in the system (gauge pressure) was 0.06 MPa; and the space velocity was 200 $h^{-1}$. After $H_2/N_2=1/5$ (volume ratio), the temperature continued to be increased at a rate of 10° C./h. When the reaction temperature reached 650° C., the sulfur content in the system was detected; when the sulfur content was equal to or greater than 0.1 ppm (by volume), the gas was switched into a thionizer 4 fed with a fine desulfurizer, e.g. ZnO, and desulfurized at a temperature of less than 800° C. for 10-12 h and fed into a water condenser 5. If the sulfur content was equal to or less than 0.1 ppm (by volume), the gas was directed switched into the water condenser 5.

Finally, the temperature in the prereduction reactor 2 was maintained at 800° C. for 3 h, wherein most of nickel was reduced. Then the temperature was decreased at a rate of 8° C./h. When the temperature inside the prereduction reactor is less than 50° C., $N_2$ was used to replace $H_2$ in the system to enable the volume percent of $H_2$ in the system to be equal to or less than 0.5%. Then $O_2$ was fed in an amount of 0.1-0.2 vol. % of the total gas amount in the system. The temperature increase was observed to ensure the temperature in the prereduction reactor to be not more than 50° C. The $O_2$ concentration was gradually increased till the temperature in the prereduction reactor was not more than 50° C. even if $O_2$ was fed. Meanwhile, after the oxygen content at the inlet of the reactor is consistent with that at the outlet, the passivation operation ends, and the prereduction also ends, which is labeled as A.

Upon analysis by X-ray diffractometer, the reduced homojunction nickel had a grain size of (111) face 10.1 nm, nickel (200) face 12.8 nm and nickel (200) face 14.9 nm.

The application of the catalyst was achieved in the fixed bed, wherein the prereduced catalyst is placed at the middle of the constant temperature zone of the reactor, and uses stainless steel net and quartz sand on the top and down as the support.

If the catalyst is not prereduced, the catalyst will be reduced in the reactor before the synthesis. The whole process lasts 5-7 days before the methane synthesis operation is conducted. The highest temperature during the reduction is 800° C., and the requirements on the materials of the whole synthesis reaction device are rather high so as to necessarily increase the product cost. After the catalyst is prereduced, said problem is solved. The prereduced catalyst is just activated at 250° C. with coke oven gas, then heated to 600° C. for the methane synthesis test, wherein the reaction pressure is 2 MPa; the space velocity is 7000 $h^{-1}$; the raw gas is the synthetic gas having a volume ratio of $H_2/CO=3/1$; the water vapor fed therein is in an amount of 20 vol. % of the raw gas; the CO conversion rate is 93.4%, and the selectivity thereof is 99.7%.

Example 2

The Catalyst Having a Composition of, in Mass Percent, 58% of $Al_2O_3$, 20% of Ni, and 22% of MgO 40 kg of nickel nitrate hexahydrate was weighted, and 40 L of distilled water was added to stir constantly until nickel nitrate hexahydrate was completely dissolved. 8.8 kg of light magnesium oxide were weighed and added to said nickel nitrate solution, heated to 60° C. at a stirring rate of 100 r/min. 30 kg of sodium metalluminate was weighed and dissolved with 370 L of distilled water to formulate 1 mol/L of sodium metalluminate solution. Sodium metalluminate having such concentration was used as the precipitator to neutralize said suspension. After completion of titration, filtering, rinsing, drying, pulverizing, sheet-beating, a catalytic body was obtained and fed into a cylindrical reactor having an aspect ratio of 3/1. A $N_2$ replacement system was used to ensure that $O_2$ in the system is in an amount of equal to or less than 0.5 vol. %, and to maintain the system pressure to be 0.03 MPa according to the pressure gauge. A compressor 7 was initiated to enable the space velocity to be 60 $h^{-1}$. The temperature was heated at a rate of 55° C./h to 120-130° C. and maintained for 3 h to clean out the physically absorbed water, then heated to 250° C. and maintained for 3 h to clean out the crystalline water, heated to 850° C. at a rate of 40° C./h and maintained for 3-6 h to enable the solid phase reaction between nickel oxide and alumina to occur and to form a nickel aluminate spinel-containing catalyst precursor.

Figure 3:
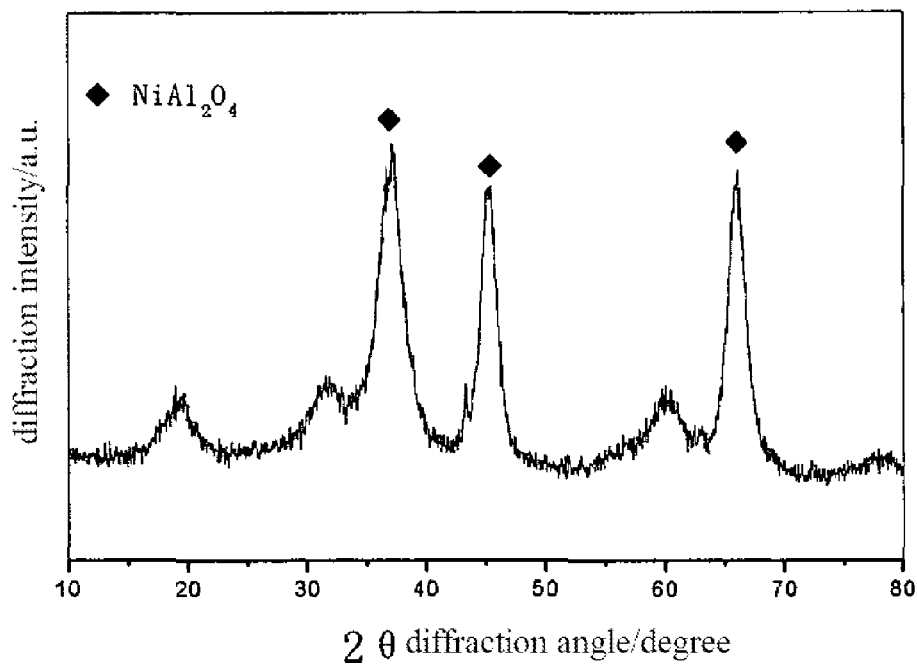
FIG. 3 shows the XRD pattern of the catalyst precursor calcined at high temperature in Example 2.

FIG. 3 shows the XRD pattern of the catalyst precursor calcined at high temperature. Thus the characteristic peaks of the nickel aluminate spinel occur, and the nickel aluminate spinel is in a mass percent of 75% in the precursor. The diffraction angles of the nickel aluminate spinel are respectively 37°, 45.1° and 65.7°.

The temperature was then decreased at a rate of 7° C./h. When the temperature inside the prereduction reactor 2 was 630° C., hydrogen was used to replace nitrogen in the system so that the pressure in the system (gauge pressure) was 0.08 MPa; and the space velocity was 400 $h^{-1}$. After $H_2/N_2=1/1$ (volume ratio), the temperature continued to be increased at a rate of 15° C./h. When the reaction temperature reached 700° C., the sulfur content in the system was detected; when the sulfur content was equal to or greater than 0.1 ppm (by volume), the gas was switched into a thionizer 4 fed with a fine desulfurizer, e.g. ZnO, and desulfurized at a temperature of less than 800° C. for 10-12 h and fed into a water condenser 5. If the sulfur content was equal to or less than 0.1 ppm (by volume), the gas was directed switched into the water condenser 5.

Finally, the temperature in the prereduction reactor 2 was maintained at 950° C. for 4 h, wherein most of nickel was reduced. Then the temperature was decreased at a rate of 15° C./h. When the temperature inside the prereduction reactor is less than 50° C., $N_2$ was used to replace $H_2$ in the system to enable the volume percent of $H_2$ in the system to be equal to or less than 0.5%. Then $O_2$ was fed in an amount of 0.1-0.2 vol. % of the total gas amount in the system. The temperature increase was observed to ensure the temperature in the prereduction reactor to be not more than 50° C. The $O_2$ concentration was gradually increased till the temperature in the prereduction reactor was not more than 50° C. even if $O_2$ was fed. Meanwhile, after the oxygen content at the inlet of the reactor is consistent with that at the outlet, the passivation operation ends, and the prereduction also ends, which is labeled as B. Upon analysis by X-ray diffractometer, the reduced homojunction nickel had a grain size of (111) face 7.0 nm, nickel (200) face 7.1 nm and nickel (200) face 7.3 nm.

The application of the catalyst was achieved in the fixed bed, wherein the prereduced catalyst is placed at the middle of the constant temperature zone of the reactor, and uses stainless steel net and quartz sand on the top and down as the support.

If the catalyst is not prereduced, the catalyst will be reduced in the reactor before the synthesis. The whole process lasts 5-7 days before the methane synthesis operation is conducted. The highest temperature during the reduction is 900° C., and the requirements on the materials of the whole synthesis reaction device are rather high so as to necessarily increase the product cost. After the catalyst is prereduced, said problem is solved. The prereduced catalyst is just activated at 250° C. with coke oven gas, then heated to 650° C., wherein the reaction pressure is 2 MPa; the space velocity is 7000 h$^{-1}$; the raw gas is the purified coke oven gas; the water vapor fed therein is in an amount of 20 vol. % of the raw gas; the CO conversion rate is 83.2%; the selectivity thereof is 99.3%; the $CO_2$ conversion rate is 70%.

Example 3

The Catalyst Having a Composition of, in Mass Percent, 65% of $Al_2O_3$, 20% of Ni, and 15% of MgO 40 kg of nickel nitrate hexahydrate was weighted, and 40 L of distilled water was added to stir constantly until nickel nitrate hexahydrate was completely dissolved. 38.5 kg of magnesium nitrate hexahydrate were weighed and added to said nickel nitrate solution, heated to 60° C. at a stirring rate of 100 r/min. 55 kg of sodium metalluminate was weighed and dissolved with 680 L of distilled water to formulate 1 mol/L of sodium metalluminate solution. Sodium metalluminate having such concentration was used as the precipitator to neutralize said suspension. After completion of titration, filtering, rinsing, drying, pulverizing, sheet-beating, a catalytic body was obtained and fed into a cylindrical reactor having an aspect ratio of 4/1. The top layer of the catalyst was fed into 10-20 cm of the prereduced catalyst as the activity initiating agent. A $N_2$ replacement system was used to ensure that $O_2$ in the system is in an amount of equal to or less than 0.5 vol. %, and to maintain the system pressure to be 0.04 MPa according to the pressure gauge. A compressor 7 was initiated to enable the space velocity to be 70 h$^{-1}$. The temperature was heated at a rate of 60° C./h to 120-130° C. and maintained for 3 h to clean out the physically absorbed water, then heated to 250° C. and maintained for 3 h to clean out the crystalline water, heated to 900° C. at a rate of 40° C./h and maintained for 3-6 h to enable the solid phase reaction between nickel oxide and alumina to occur and to form a nickel aluminate spinel-containing catalyst precursor.

Figure 4:
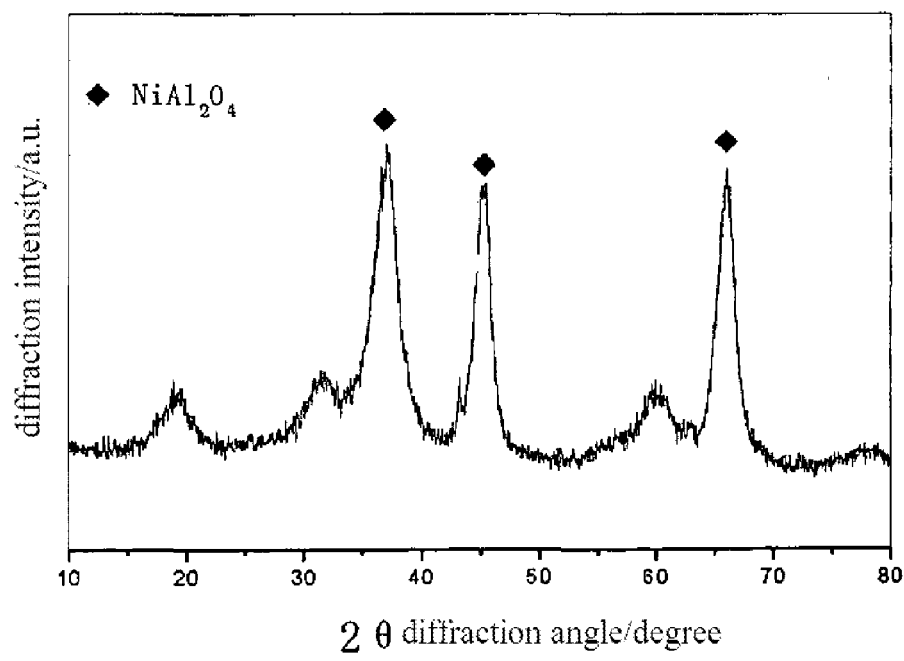
FIG. 4 shows the XRD pattern of the catalyst precursor calcined at high temperature in Example 3.

FIG. 4 shows the XRD pattern of the catalyst precursor calcined at high temperature. Thus the characteristic peaks of the nickel aluminate spinel occur, and the nickel aluminate spinel is in a mass percent of 56% in the precursor. The diffraction angles of the nickel aluminate spinel are respectively 37°, 45.1° and 65.7°.

The temperature was then decreased at a rate of 8° C./h. When the temperature inside the prereduction reactor 2 was 650° C., hydrogen was used to replace nitrogen in the system so that the pressure in the system (gauge pressure) was 0.09 MPa; and the space velocity was 600 h$^{-1}$. After $H_2/N_2$=5/1 (volume ratio), the temperature continued to be increased at a rate of 20° C./h. When the reaction temperature reached 750° C., the sulfur content in the system was detected; when the sulfur content was equal to or greater than 0.1 ppm (by volume), the gas was switched into a thionizer 4 fed with a fine desulfurizer, e.g. ZnO, and desulfurized at a temperature of less than 800° C. for 10-12 h and fed into a water condenser 5. If the sulfur content was equal to or less than 0.1 ppm (by volume), the gas was directed switched into the water condenser 5.

Finally, the temperature in the prereduction reactor 2 was maintained at 1000° C. for 5 h, wherein most of nickel was reduced. Then the temperature was decreased at a rate of 20° C./h. When the temperature inside the prereduction reactor is less than 50° C., $N_2$ was used to replace $H_2$ in the system to enable the volume percent of $H_2$ in the system to be equal to or less than 0.5%. Then $O_2$ was fed in an amount of 0.1-0.2 vol. % of the total gas amount in the system. The temperature increase was observed to ensure the temperature in the prereduction reactor to be not more than 50° C. The $O_2$ concentration was gradually increased till the temperature in the prereduction reactor was not more than 50° C. even if $O_2$ was fed. Meanwhile, after the oxygen content at the inlet of the reactor is consistent with that at the outlet, the passivation operation ends, and the prereduction also ends, which is labeled as C. Upon analysis by X-ray diffractometer, the reduced homojunction nickel had a grain size of (111) face 9.4 nm, nickel (200) face 11.3 nm and nickel (200) face 13.5 nm.

The application of the catalyst was achieved in the fixed bed, wherein the prereduced catalyst is placed at the middle of the constant temperature zone of the reactor, and uses stainless steel net and quartz sand on the top and down as the support.

If the catalyst is not prereduced, the catalyst will be reduced in the reactor before the synthesis. The whole process lasts 5-7 days before the methane synthesis operation is conducted. The highest temperature during the reduction is 1000° C., and the requirements on the materials of the whole synthesis reaction device are rather high so as to necessarily increase the product cost. After the catalyst is prereduced, said problem is solved. The prereduced catalyst is just activated at 250° C. with coke oven gas, then heated to 700° C., wherein the reaction pressure is 2 MPa; the space velocity is 7000 h$^{-1}$; the raw gas comprises in volume, 12.5% of CO, 10% of $CO_2$, and 77.5% of $H_2$. The water vapor fed therein is in an amount of 20 vol. % of the raw gas. Upon measurement, the CO conversion rate is 79.9%; the selectivity thereof is 99.5%; the $CO_2$ conversion rate is 66.5%.

Example 4

After the reaction of various catalysts for 720 h, the activities of various catalysts are not notably changed. After the reaction stops, and the catalysts are discharged, XRD and DTG analyses are conducted for comparison.

| Catalyst | | A | B | C |
|---|---|---|---|---|
| XRD | Presence of absence of hydration peak | Absence of hydration peak | Absence of hydration peak | Absence of hydration peak |
| | Ni grain size before reaction | (111) face 10.1 nm (200) face 12.8 nm (220) face 14.9 nm | (111) face 9.4 nm (200) face 11.3 nm (220) face 13.5 nm | (111) face 7.0 nm (200) face 7.1 nm (220) face 7.3 nm |
| | Ni grain size after reaction | (111) face 10.2 nm (200) face 13.0 nm (220) face 15.0 nm | (111) face 9.5 nm (200) face 11.5 nm (220) face 13.7 nm | (111) face 7.0 nm (200) face 7.3 nm (220) face 7.4 nm |
| DTG Carbon content (vol. %) in the used catalyst | | Not detected | Not detected | Not detected |

The invention claimed is:

1. A method for preparing a methane synthesis catalyst, comprising a preparation step for a catalytic body containing nickel nitrate, an aluminium compound and a magnesium compound and a prereduction step, wherein the catalytic body is produced by the mixing-precipitation method or the coprecipitation method; the prereduction step comprises calcining the catalytic body at 700-1100° C. to form a nickel aluminate spinel-containing catalyst precursor; and prereducing the catalyst precursor at 700-1000° C. to acquire the methane synthesis catalyst;
wherein the prereduction step is conducted in a prereduction reactor at a system pressure of 0.05-0.1 MPa and a space velocity of 100-800 $h^{-1}$.

2. The preparation method according to claim 1, wherein the preparation step for a catalytic body by the mixing-precipitation method comprises spray drying a slurry containing nickel nitrate, aluminium hydroxide and light magnesium oxide.

3. The preparation method according to claim 1, wherein the preparation step for a catalytic body by the coprecipitation method comprises neutralizing with an aluminium-containing precipitator a suspension or solution containing nickel nitrate and a magnesium compound selected from the group consisting of magnesium nitrate and light magnesium oxide.

4. The preparation method according to claim 3, wherein the aluminium-containing precipitator is sodium metaaluminate.

5. The preparation method according to claim 1, wherein the calcining step comprises using a $N_2$ replacement system to ensure that $O_2$ in the system is in an amount of equal to or less than 0.5 vol. %, maintaining the system pressure to be 0.01-0.05 MPa according to a pressure gauge, a space velocity being 50-100 $h^{-1}$, heating to 120-130° C. at a rate of 50-70° C./h, maintaining the temperature for 2-5 h to clean out physically absorbed water, continuing to heat to 250° C. at a rate of 30-70° C./h, maintaining the temperature for 2-5 h to clean out crystalline water, continuing to heat to 700-1000° C. at a rate of 10-70° C./h, maintaining the temperature for 3-6 h to form a nickel aluminate spinel-containing catalyst precursor.

6. The preparation method according to claim 1, wherein the prereduction step further comprises the step of desulfurizing the catalyst, the desulfurizing step comprising detecting a sulfur content in a reduction gas of the system while the reaction temperature in the prereduction reactor reaches 650-750° C., the gas being switched to a thionizer if the volume content of sulfur in the reduction gas of the reduction system is equal to or more than 0.1 ppm, desulfurizing at a temperature less than 800° C. for 10-12 h so as to desulfurize the catalyst.

7. The preparation process according to claim 1, wherein the methane synthesis catalyst, comprises, in mass percent, 40-80% of $Al_2O_3$, 10-30% of Ni, and 10-30% of MgO.

8. The preparation process according to claim 1, wherein $H_2$ is used as a reduction gas in the prereduction step, and $H_2/N_2=1/10$-$10/1$ by volume.

9. The preparation process according to claim 1, further comprising the following termination steps of reducing the internal temperature inside the prereduction reactor, replacing $N_2$ with reduction gas in a reactor while internal temperature in the prereduction reactor is lowered to less than 50° C., to make a volume content of $H_2$ in the reactor equal to or less than 0.5%; feeding $O_2$ till $O_2$ is in a volume amount of 0.1-0.2% of the total gas in the reactor, while maintaining the temperature inside the prereduction reactor at not more than 50° C.; feeding air and maintaining the temperature inside the reactor at not more than 50° C. till the oxygen content at an inlet of the reactor is consistent with the oxygen content at an outlet of the reactor.

* * * * *